(12) United States Patent
Chang et al.

(10) Patent No.: US 10,241,020 B2
(45) Date of Patent: Mar. 26, 2019

(54) ATMOSPHERIC PARTICLE COUNTING

(71) Applicant: International Business Machines Corporation, Armonk, NY (US)

(72) Inventors: Josephine B. Chang, Ellicott City, MD (US); Hendrik F. Hamann, Yorktown Heights, NY (US); Ramachandran Muralidhar, Mahopac, NY (US); Theodore G. van Kessel, Millbrook, NY (US); Jun Song Wang, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/853,128

(22) Filed: Dec. 22, 2017

(65) Prior Publication Data

US 2018/0209888 A1 Jul. 26, 2018

Related U.S. Application Data

(63) Continuation of application No. 15/238,412, filed on Aug. 16, 2016, now Pat. No. 9,933,350.

(51) Int. Cl.
*G01N 15/06* (2006.01)
*G01N 15/02* (2006.01)
(Continued)

(52) U.S. Cl.
CPC ......... *G01N 15/06* (2013.01); *G01N 15/0205* (2013.01); *G01N 15/1459* (2013.01);
(Continued)

(58) Field of Classification Search
CPC .......... G01N 33/0031; G01N 15/0205; G01N 15/06; G01N 33/0075; G01N 21/53;
(Continued)

(56) References Cited

U.S. PATENT DOCUMENTS 3,921,192 A 11/1975 Goronkin et al.
4,281,924 A 8/1981 Auer et al.
(Continued)

OTHER PUBLICATIONS

Huebert et al., "PELTI: Measuring the passing efficiency of an airborne low turbulence aerosol inlet," Aerosol Science and Technology, vol. 38, No. 8, Jun. 2004, pp. 803-826.
(Continued)

*Primary Examiner* — Michael P Stafira
(74) *Attorney, Agent, or Firm* — Vazken Alexanian; Michael J. Chang, LLC (57) ABSTRACT

Atmospheric particle detectors having a hybrid measurement cavity and light baffle are provided. In one aspect, an atmospheric particle detector includes: an optical measurement cavity; a light baffle attached to the optical measurement cavity, wherein the light baffle is configured to i) permit unobstructed airflow into the optical measurement cavity and ii) block ambient light from entering the optical measurement cavity; a photodetector on a first side of the optical measurement cavity; a retro reflector on a second side of the optical measurement cavity opposite the photodetector, and a light source configured to produce a light beam that passes through the optical measurement cavity without illuminating the photodetector. A method for particle detection using the atmospheric particle detector is also provided.

20 Claims, 5 Drawing Sheets

(51) Int. Cl.
*G01N 21/53* (2006.01)
*G01N 15/14* (2006.01)
*G01N 15/00* (2006.01)

(52) U.S. Cl.
CPC ......... *G01N 21/53* (2013.01); *G01N 15/0211* (2013.01); *G01N 2015/0046* (2013.01); *G01N 2015/0693* (2013.01); *G01N 2015/1486* (2013.01); *G01N 2201/068* (2013.01); *G01N 2201/0636* (2013.01)

(58) Field of Classification Search
CPC ............... G01N 21/84; G01N 15/1434; G01N 2015/0693; G01N 33/00; G01N 15/1459; G01N 30/74; G01N 2201/062; G01N 2015/0046; G01N 21/49
See application file for complete search history.

(56) References Cited

U.S. PATENT DOCUMENTS

| | | |
|---|---|---|
| 4,728,190 A | 3/1988 | Knollenberg |
| 5,428,443 A | 6/1995 | Kitamura et al. |
| 6,167,107 A | 12/2000 | Bates |
| 6,414,754 B1 | 7/2002 | Johnson |
| 6,903,818 B2 | 6/2005 | Cerni et al. |
| 7,631,568 B2 | 12/2009 | Kilps et al. |
| 8,427,642 B2 | 4/2013 | Mitchell et al. |
| 2013/0229655 A1* | 9/2013 | Kaye ............... G01N 15/0205 356/343 |
| 2015/0063982 A1* | 3/2015 | Pariseau ............ F04D 19/022 415/115 |

OTHER PUBLICATIONS

List of IBM Patents or Applications Treated as Related (2 pages).

* cited by examiner

ATMOSPHERIC PARTICLE COUNTING

CROSS-REFERENCE TO RELATED APPLICATIONS

This application is a continuation of U.S. application Ser. No. 15/238,412 filed on Aug. 16, 2016, now U.S. Pat. No. 9,933,350, the disclosure of which is incorporated by reference herein.

FIELD OF THE INVENTION

The present invention relates to atmospheric particle detectors, and more particularly, to atmospheric particle detectors having a hybrid measurement cavity and light baffle and techniques for use thereof.

BACKGROUND OF THE INVENTION

Atmospheric particle counting is an important component of overall pollution monitoring. The data on particle size and concentration are essential to air pollution source identification and forecasting.

Many cities and urban areas have evolved highly polluted atmospheres. Accordingly, it is desirable to have a large number of sensors operating autonomously to collect long term, high resolution (concentrated) data. However, due to high levels of pollution, the sensor devices need to be resilient to particle build-up in order to afford long term service.

Accordingly, a particle counter that collects long term, high resolution data even in highly polluted atmospheres would be desirable.

SUMMARY OF THE INVENTION

The present invention provides atmospheric particle detectors having a hybrid measurement cavity and light baffle and techniques for use thereof. In one aspect of the invention, an atmospheric particle detector is provided. The atmospheric particle detector includes: an optical measurement cavity; a light baffle attached to the optical measurement cavity, wherein the light baffle is configured to i) permit unobstructed airflow into the optical measurement cavity and ii) block ambient light from entering the optical measurement cavity; a photodetector on a first side of the optical measurement cavity; a retro reflector on a second side of the optical measurement cavity opposite the photodetector; and a light source configured to produce a light beam that passes through the optical measurement cavity without illuminating the photodetector.

In another aspect of the invention, a method for particle detection is provided. The method includes: providing an atmospheric particle detector, comprising: an optical measurement cavity, a light baffle attached to the optical measurement cavity, a photodetector on a first side of the optical measurement cavity, a retro reflector on a second side of the optical measurement cavity opposite the photodetector, and a light source configured to produce a light beam that passes through the optical measurement cavity without illuminating the photodetector; introducing an air sample into the optical measurement cavity through the light baffle, wherein the light baffle permits unobstructed airflow into the optical measurement cavity and blocks ambient light from entering the optical measurement cavity; passing the light beam through the air sample in the optical measurement cavity between the photodetector and the retro reflector, wherein light from the light beam is scattered off of particles in the air sample to the photodetector or to the retro reflector which reflects the light back toward the photodetector; and detecting the light scattered off of the particles using the photodetector.

A more complete understanding of the present invention, as well as further features and advantages of the present invention, will be obtained by reference to the following detailed description and drawings.

DETAILED DESCRIPTION OF PREFERRED EMBODIMENTS

A light- or laser-based optical particle counter operates by providing a constant sample airflow through an optical cavity where the airflow passes through a light/laser beam. Light scatters off of the particles in the airflow sample and this scattering is detected by a photodetector. Over an extended period of time, however, with conventional optical particle counters particles build up on the walls of the optical cavity causing a constant level of scattered light to be created. This constant accumulation eventually builds up to the point that the instrument is inoperable. In high pollution areas, this accumulation can occur quite rapidly.

Provided herein are light- or laser-based particle counting devices wherein a sample airflow cavity is constructed so as to allow outside air to diffuse in through a light baffle or to be actively drawn in according to the air particle concentration and the desired measurement interval. Advantageously, this light-baffled and optional active pump design, allows for managing the amount of air ingested (i.e., drawn into) in the optical cavity to minimize the amount of particle accumulation.

Minimization of particle accumulation can be accomplished by coating exposed surfaces with hydrophobic materials (see below), designing the optical cavity to eliminate fluid stagnation points with respect to the airflow, and most fundamentally reducing the amount of ingested air. For a given cavity configuration and ambient particle concentration, it is reasonable to conclude that lifetime is proportional to the volume of ingested air.

Further, as will be described in detail below, one can thus adjust the amount of air ingested into the device based on the particle content being observed to minimize the amount of exposure of the optical cavity to pollution. For instance, as the particle count increases due to high pollution, the air sample size can be decreased accordingly to prevent over contamination of the device.

Also, given the goal of operating the device remotely and over extended periods of time, it is desirable to minimize the overall power consumption of the device. As will be described in detail below, embodiments are provided herein where low power consumption components are employed, such as a micro diaphragm pump that consumes, e.g., about 40 milliamps of current at 3.3 volts.

Therefore, the present particle detection device is optimal for long life in highly polluted environments in that: 1) the device is able to operate by diffusion only (or optionally under active pumping; 2) the device can operate by drawing one cavity volume of air at a time to reduce the time to equilibrium with the outside air; and 3) when air is drawn continuously, it can be for short precise durations.

Figure 1:
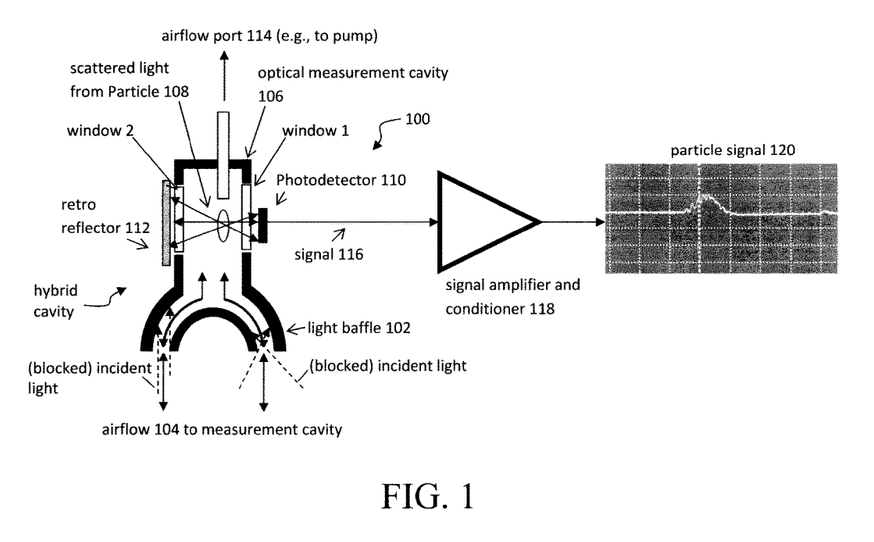
FIG. 1 is a diagram illustrating an exemplary atmospheric particle detector according to an embodiment of the present invention.

FIG. 1 is a diagram illustrating an atmospheric particle detector 100 according to an exemplary embodiment. Particle detector 100 includes a hybrid airflow intake/optical measurement cavity that is open to the external environment. Namely, as shown in FIG. 1, the hybrid cavity has a light baffle 102 that is open to airflow 104 from the external environment but which blocks ambient light from entering the optical measurement cavity 106. The optical measurement cavity 106 is connected to the light baffle 102 such that outside airflow 104 can diffuse or be actively pumped/drawn into the optical measurement cavity 106. The optical measurement cavity 106 is configured such that a light or laser beam from a light source (see FIG. 2—described below) can be transmitted through the optical measurement cavity 106 whereby particles entrained in the air sample within the optical measurement cavity 106 scatter light 108 in detectable view of a photodetector 110 and/or to a retro reflector 112 (located on a side of the optical measurement cavity 106 opposite the photodetector 110) which reflects the light back towards the photodetector 110.

According to an exemplary embodiment, the photodetector 110 includes a photodiode, an avalanche diode, and/or a photomultiplier tube. Photodiodes convert light into current when photons are absorbed in the photodiode. An avalanche diode is a semiconductor-based diode in which avalanche multiplication of charge carriers occurs. See, for example, U.S. Pat. No. 3,921,192 issued to Goronkin et al., entitled "Avalanche Diode," the contents of which are incorporated by reference as if fully set forth herein. Photomultiplier tubes operate by amplifying electrons generated by a photocathode that are exposed to a photon flux.

The optical measurement cavity 106 is transparent to light. Namely, as shown in FIG. 1, the scattered light 108 within the optical measurement cavity 106 can pass through a first transparent window (labeled "window 1") toward the photodetector 110 and/or through a second transparent window (labeled "window 2") toward the retro reflector 112. According to an exemplary embodiment, first transparent window 1 and second transparent window 2 are located on opposite sides of the optical measurement cavity 106 in line of sight of one another. That way, light is reflected off of the retro reflector 112 back towards the photodetector 110 (thereby amplifying the signal 116). The first transparent window 1 and second transparent window 2 preferably form an airtight seal with the walls of the optical measurement cavity 106 thereby limiting airflow into the optical measurement cavity 106 to that through the light baffle 102. Suitable materials for forming the first transparent window 1 and the second transparent window 2 include, but are not limited to, glass, transparent plastics, etc.

According to an exemplary embodiment, inner surfaces of the optical measurement cavity 106 are lined with a super hydrophobic coating to minimize the attachment and accumulation of particles on the walls and/or other surfaces of the cavity. By way of example only, the super hydrophobic coating can include a monolayer (i.e., a layer that is one atom thick) of a fluorinated silated compound. Examples include a variety of surface-modifying compounds offered by Gelest, Inc., Morrisville, Pa. such as fluoroalkylsilanes: SIT8371.0 ((3,3,3-trifluoropropyl) trichlorosilane), SIT8174.0 ((tridecafluoro-1,1,2,2-tetrahydrooctyl) trichlorosilane), and/or SIH5841.0 ((heptadecafluoro-1,1,2,2-tetrahydrodecyl) trichlorosilane) that can be applied to form a surface layer on the inner walls of the cavity.

As shown in FIG. 1, the scattered light 108 within the optical measurement cavity 106 is further directed to the photodetector 110 by a retro reflector 112 thereby increasing the size of the scattered light signal. The term "retro reflector" as used herein generally refers to any means for reflecting light back towards its source. According to an exemplary embodiment, the retro reflector 112 includes a reflective tape, reflective paint and/or a reflective composite material. Examples of these materials include tapes and paints (often used in roadway reflectors) that incorporate titanated (some fraction of titanium oxide) glass spheres. By including titanium oxide in the glass formulation, it is possible to achieve an optical index close to 2.0. A sphere with this optical index will retro reflect from its rear surface. The reflection at the back interface of the sphere is often enhanced by using an adhesive that favorably affects the index mismatch with respect to the sphere. Alternative embodiments of retro reflectors include tapes with a first surface of clear plastic embossed with prismatic tessellations that retro reflect light similar to corner reflectors.

The light baffle 102 is configured to permit (unobstructed) airflow into the optical measurement cavity 106 while at the same time block outside light from entering the optical measurement cavity 106. For instance, in the example shown illustrated in FIG. 1, the light baffle 102 is a semi-circular-shaped conduit which freely permits airflow into or out of the optical measurement cavity 106. However, as shown in FIG. 1, light cannot enter the optical measurement cavity 106 through the light baffle 102. Preferably, the interior surfaces of the light baffle 102 are non-reflective, e.g., lined with a non-reflective coating, so as to prevent reflection of incident light into the cavity.

A port 114 is connected to the hybrid cavity to allow an external air pump (see, e.g., FIG. 2—described below) to serve as an optional means for actively drawing air into the cavity. Suitable air pumps include, but are not limited to, micro diaphragm pumps, micro peristaltic pumps, and/or micro positive displacement pumps. As provided above, for long term service it is desirable for the device to consume minimal amounts of power during operation. For instance, a micro diaphragm pump consumes less than or equal to about 40 mA of current at about 3.3 volts. Suitable micro diaphragm pumps are available commercially, e.g., from Parker-Hannifin, Cleveland, Ohio.

Light incident to the photodetector 110 causes an electrical signal 116 to be produced. As shown in FIG. 1, this signal is further amplified and conditioned by a circuit 118 to produce a detectable pulse 120 that is ultimately digitized, measured and counted. The data so produced is used to estimate the particle size and concentration in the immediate environment.

Figure 2:
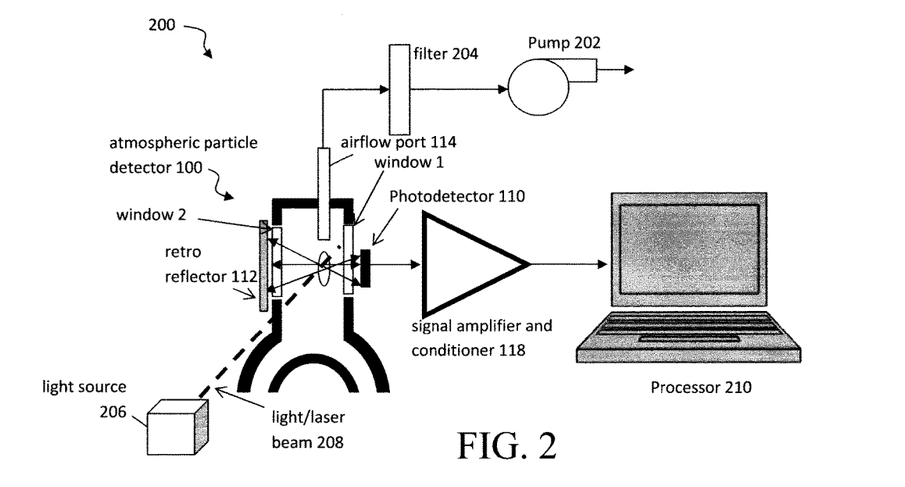
FIG. 2 is a diagram illustrating an exemplary system incorporating the atmospheric particle detector of FIG. 1 according to an embodiment of the present invention.

An exemplary system 200 is shown illustrated in FIG. 2 that incorporates the atmospheric particle detector 100 of FIG. 1. As shown in FIG. 2, the airflow port 114 can be connected to (at least one) air pump 202. As provided above, a suitable air pump includes a micro diaphragm pump, a micro peristaltic pump, and/or a micro positive displacement pump.

Preferably, a filter 204 is present between the airflow port 114 and the air pump 202 to capture particles exiting the atmospheric particle detector 100 via the airflow port 114. Namely, as will be described in detail below, several different modes of operation may be employed. In one mode, simple diffusion of the airflow sample into the optical measurement cavity 106 is employed. See, e.g., FIG. 3—described below. In that case, no action of the air pump 202 is needed.

In another mode, the air pump 202 is used to actively draw the air sample into the optical measurement cavity 106. Specifically, the air pump 202 can be used to draw air out of the optical measurement cavity 106 via the airflow port 114 which serves to draw outside air into the optical measurement cavity 106 via the light baffle 102. In one exemplary embodiment, the air pump 202 is used to draw a measured amount (which can be regulated based on the length of time the air pump 202 is turned on) of an air sample into the optical measurement cavity 106—after which the pump is turned off. See, e.g., FIG. 4—described below. Alternatively, in another exemplary embodiment, the air pump 202 is operated continuously generating a constant airflow sample through the optical measurement cavity 106. See, e.g., FIG. 5—described below.

FIG. 2 also illustrates how a light source 206 can be positioned to introduce a light or laser beam 208 into the optical measurement cavity 106. Namely, the light source 206 can be located within the optical measurement cavity 106 or outside of the optical measurement cavity 106, as long as the light or laser beam 208 passes between the first transparent window (labeled "window 1") and the second transparent window (labeled "window 2") in line of sight of the photodetector 110. Suitable light sources 208 include, but are not limited to, a diode laser, a gas laser, a light emitting diode (LED) and/or an incandescent source. It is notable that, as shown in FIG. 2, the light or laser beam 208 produced by the light source 206 passes through the optical measurement cavity 106 in a manner so as to illuminate the optical measurement cavity 106 and thus the particles within the optical measurement cavity 106, but not illuminate the photodetector 110. As described above, it is the light from beam 208 that is scattered by the particles in the air sample that illuminates the photodetector 110 (and/or the scattered light reflected back by the retro reflector). To do so, as shown in FIG. 2, the beam 208 can pass perpendicular to the line of sight between the photodetector 110 and the retro reflector 112. In the exemplary embodiment shown in FIG. 2, a processor 210 (such as apparatus 700 with data processing capabilities—see for example FIG. 7, described below) is used to digitize the conditioned signal from circuit 118.

As provided above, the present atmospheric particle detector system can be operated in different modes. For instance, in one (first) mode passive air diffusion and Brownian motion through the light baffle 102 is used to introduce air samples into the optical measurement cavity 106. See, e.g., methodology 300 of FIG. 3. Namely, the light baffle is open to outside air and in step 302 air simply diffuses into the optical measurement cavity 106.

Figure 3:
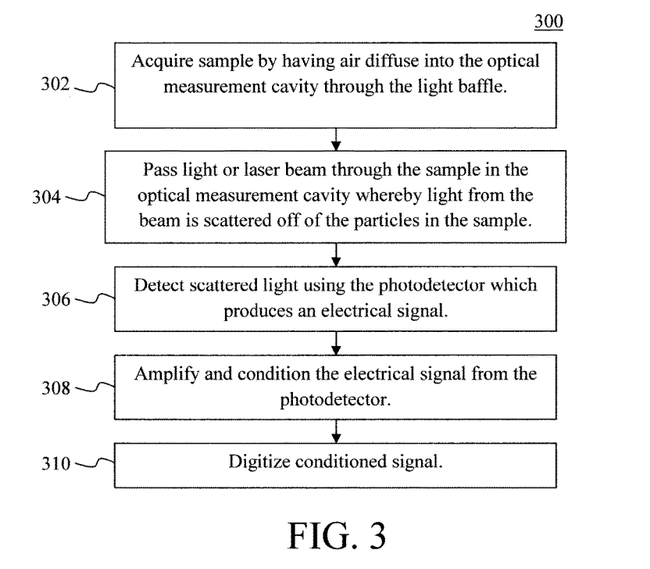
FIG. 3 is a diagram illustrating an exemplary methodology for particle detection using the present atmospheric particle detector and simple diffusion of air samples into the detector according to an embodiment of the present invention.

In step 304, the light or laser beam 208 is passed through the air sample in the optical measurement cavity 106 and light from the beam 208 is scattered off of the particles in the air sample. In step 306, the scattered light is detected by the photodetector 110 which produces an electrical signal. As described above, the retro reflector 112 reflects light scattered in the optical measurement cavity 106 back toward the photodetector 110.

In step 308, the electrical signal from the photodetector 110 is amplified and conditioned using the circuit 118. In step 310, the conditioned signal is digitized and processed by processor 210.

Figure 4:
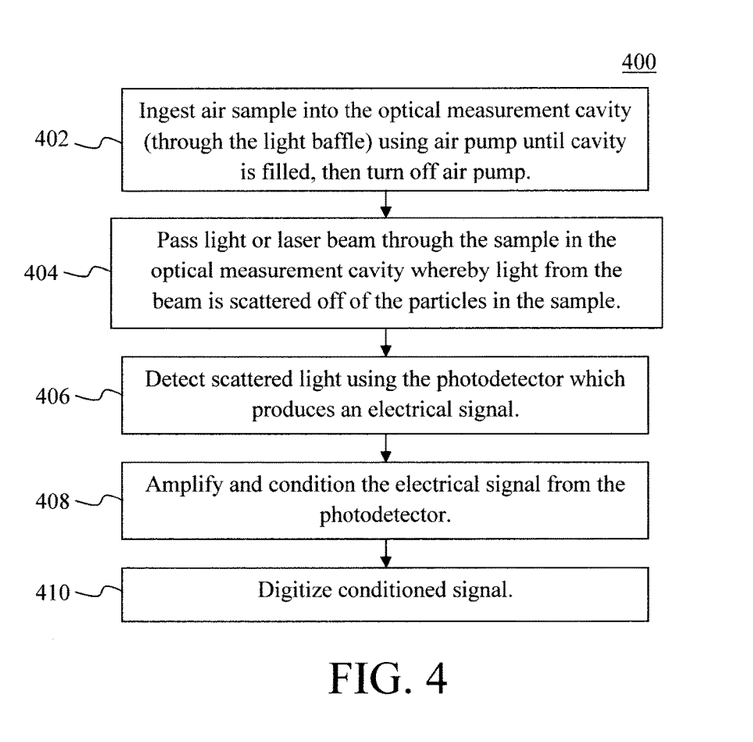
FIG. 4 is a diagram illustrating an exemplary methodology for particle detection using the present atmospheric particle detector and active ingestion of a measured amount of air sample using an air pump according to an embodiment of the present invention.

In another exemplary (second) mode of operation described by way of reference to methodology 400 of FIG. 4, air is ingested into the optical measurement cavity 106 (through the light baffle 102) using air pump 202 and, after an amount of air sufficient to fill the cavity is ingested into the optical measurement cavity 106, the air pump 202 is stopped. See step 402. The particle detection then proceeds in the same manner as described above.

Namely, in step 404, the light or laser beam 208 is passed through the air sample in the optical measurement cavity 106 and light from the beam 208 is scattered off of the particles in the air sample. In step 406, the scattered light is detected by the photodetector 110 which produces an electrical signal. As described above, the retro reflector 112 reflects light scattered in the optical measurement cavity 106 back toward the photodetector 110.

In step 408, the electrical signal from the photodetector 110 is amplified and conditioned using the circuit 118. In step 410, the conditioned signal is digitized and processed by processor 210.

Figure 5:
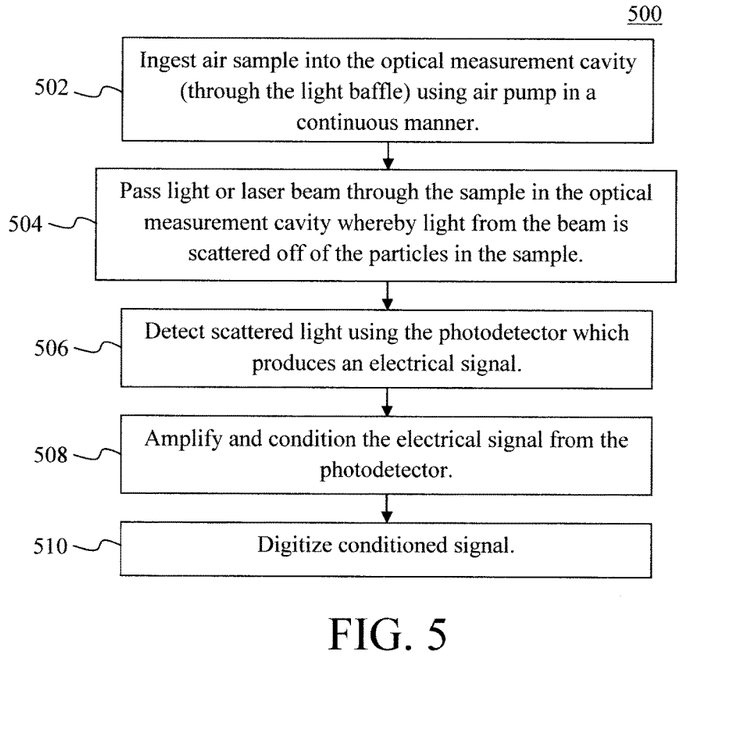
FIG. 5 is a diagram illustrating an exemplary methodology for particle detection using the present atmospheric particle detector and continuous active ingestion of air samples using an air pump according to an embodiment of the present invention.

In yet another exemplary (third) mode of operation described by way of reference to methodology 500 of FIG. 5, air is ingested into the optical measurement cavity 106 (through the light baffle 102) using air pump 202 and is processed continuously. See step 502. By comparison with methodologies 300 and 400 described above which use diffusion and Brownian motion, in methodology 500 particles move through the optical measurement cavity 106 at a velocity proportional to the pump speed and the size of the optical measurement cavity 106. The particle detection is performed in the same manner as described above. It is notable that the air sampling (step 502) and the particle detection (steps 504-510) are performed simultaneously and continuously in this example.

Namely, in step 504, the light or laser beam 208 is passed through the air sample in the optical measurement cavity 106 and light from the beam 208 is scattered off of the particles in the air sample. In step 506, the scattered light is detected by the photodetector 110 which produces an electrical signal. As described above, the retro reflector 112 reflects light scattered in the optical measurement cavity 106 back toward the photodetector 110.

In step 508, the electrical signal from the photodetector 110 is amplified and conditioned using the circuit 118. In step 510, the conditioned signal is digitized and processed by processor 210.

The detected particles in the third mode (i.e., methodology 500) have a narrower pulse width than those detected in the first and second modes (i.e., methodologies 300 and 400). Each mode of operation can be beneficial for a given set of conditions. For instance, the third mode (i.e., methodology 500) is preferable in low particle concentration environments. The first and second modes (i.e., methodologies 300 and 400) are preferable in medium to high particle concentration environments.

Figure 6:
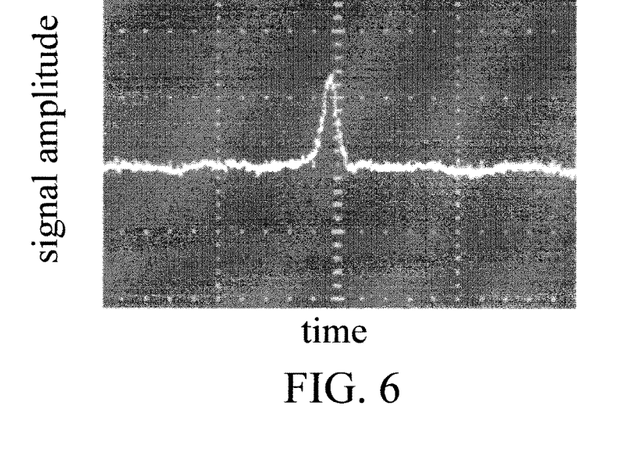
FIG. 6 is a diagram illustrating a detected light pulse from laser light scattered from particles according to an embodiment of the present invention.

FIG. 6 is a diagram illustrating an electrical signal generated by the photodetector 110. As shown in FIG. 6, the signal amplitude is plotted as a function of time. As provided above, suitable photodetectors include, but are not limited to, photodiodes, avalanche diodes, and/or photomultiplier tubes.

Figure 7:
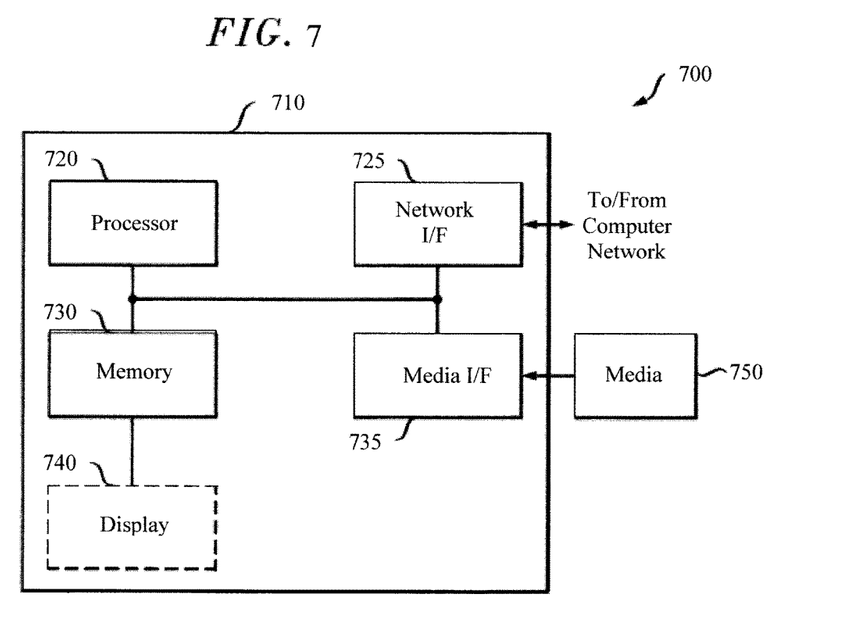
FIG. 7 is a diagram illustrating an exemplary apparatus that can be implemented to serve as the processor in the system of FIG. 2 according to an embodiment of the present invention.

Turning now to FIG. 7, a block diagram is shown of an apparatus 700 that can be implemented to serve as processor 210 (see FIG. 2, described above). Apparatus 700 includes a computer system 710 and removable media 750. Computer system 710 includes a processor device 720, a network interface 725, a memory 730, a media interface 735 and an optional display 740. Network interface 725 allows computer system 710 to connect to a network, while media interface 735 allows computer system 710 to interact with media, such as a hard drive or removable media 750.

Processor device 720 can be configured to implement the methods, steps, and functions disclosed herein. The memory 730 could be distributed or local and the processor device 720 could be distributed or singular. The memory 730 could be implemented as an electrical, magnetic or optical memory, or any combination of these or other types of storage devices. Moreover, the term "memory" should be construed broadly enough to encompass any information able to be read from, or written to, an address in the addressable space accessed by processor device 720. With this definition, information on a network, accessible through network interface 725, is still within memory 730 because the processor device 720 can retrieve the information from the network. It should be noted that each distributed processor that makes up processor device 720 generally contains its own addressable memory space. It should also be noted that some or all of computer system 710 can be incorporated into an application-specific or general-use integrated circuit.

Optional display 740 is any type of display suitable for interacting with a human user of apparatus 700. Generally, display 740 is a computer monitor or other similar display Although illustrative embodiments of the present invention have been described herein, it is to be understood that the invention is not limited to those precise embodiments, and that various other changes and modifications may be made by one skilled in the art without departing from the scope of the invention.

What is claimed is:

1. An atmospheric particle detector, comprising:
an optical measurement cavity;
a light baffle attached to the optical measurement cavity, wherein the light baffle is configured to i) permit unobstructed airflow into the optical measurement cavity and ii) block ambient light from entering the optical measurement cavity, wherein the light baffle comprises a conduit attached to an opening of the optical measurement cavity that directs the airflow into the optical measurement cavity along semicircular pathways that converge at the opening of the optical measurement cavity;
a photodetector on a first side of the optical measurement cavity;
a retro reflector on a second side of the optical measurement cavity opposite the photodetector; and
a light source configured to produce a light beam that passes through the optical measurement cavity without illuminating the photodetector.

2. The atmospheric particle detector of claim 1, wherein interior surfaces of the light baffle are lined with a non-reflective coating.

3. The atmospheric particle detector of claim 1, wherein the photodetector is selected from the group consisting of: a photodiode, an avalanche diode, a photomultiplier tube, and combinations thereof.

4. The atmospheric particle detector of claim 1, wherein the light source is selected from the group consisting of: a diode laser, a gas laser, a light emitting diode (LED), an incandescent source, and combinations thereof.

5. The atmospheric particle detector of claim 1, further comprising:
a first transparent window in the first side of the optical measurement cavity through which light can pass between the optical measurement cavity and the photodetector; and
a second transparent window in the second side of the optical measurement cavity through which light can pass between the optical measurement cavity and the retro reflector.

6. The atmospheric particle detector of claim 1, wherein an inner surface of the optical measurement cavity is lined with a super hydrophobic coating.

7. The atmospheric particle detector of claim 6, wherein the super hydrophobic coating comprises a fluoroalkylsilane selected from the group consisting of: 3,3,3-trifluoropropyl trichlorosilane, (tridecafluoro-1,1,2,2-tetrahydrooctyl) trichlorosilane, (heptadecafluoro-1,1,2,2-tetrahydrodecyl) trichlorosilane, and combinations thereof.

8. The atmospheric particle detector of claim 1, wherein the retro reflector is selected from the group consisting of: reflective tape, reflective paint, a reflective composite material, and combinations thereof.

9. The atmospheric particle detector of claim 1, further comprising:
an air pump connected to the optical measurement cavity via an airflow port.

10. The atmospheric particle detector of claim 9, wherein the air pump is selected from the group consisting of: a micro diaphragm pump, a micro peristaltic pump, and a micro positive displacement pump.

11. The atmospheric particle detector of claim 9, further comprising:
a filter between the optical measurement cavity and the air pump.

12. The atmospheric particle detector of claim 1, further comprising:
a signal conditioner configured to condition electrical signals from the photodetector; and
a processor configured to digitize the electrical signals from the signal conditioner.

13. A method for particle detection, comprising:
providing an atmospheric particle detector, comprising: an optical measurement cavity, a light baffle attached to the optical measurement cavity, a photodetector on a first side of the optical measurement cavity, a retro reflector on a second side of the optical measurement cavity opposite the photodetector, and a light source configured to produce a light beam that passes through the optical measurement cavity without illuminating the photodetector;
introducing an air sample into the optical measurement cavity through the light baffle, wherein the light baffle permits unobstructed airflow into the optical measurement cavity and blocks ambient light from entering the optical measurement cavity, and wherein the light baffle comprises a conduit attached to an opening of the optical measurement cavity that directs the air sample into the optical measurement cavity along semicircular pathways that converge at the opening of the optical measurement cavity;

passing the light beam through the air sample in the optical measurement cavity between the photodetector and the retro reflector, wherein light from the light beam is scattered off of particles in the air sample to the photodetector or to the retro reflector which reflects the light back toward the photodetector; and detecting the light scattered off of the particles using the photodetector.

14. The method of claim 13, wherein the photodetector, upon detecting the light scattered off of the particles, produces an electrical signal, the method further comprising:
conditioning the electrical signal; and
digitizing the electrical signal.

15. The method of claim 13, wherein the air sample is permitted to diffuse into the optical measurement cavity through the light baffle.

16. The method of claim 13, wherein the atmospheric particle detector further comprises an air pump connected to the optical measurement cavity via an airflow port, the method further comprising:

drawing the air sample into the optical measurement cavity using the air pump; and turning off the air pump once the air sample fills the optical measurement cavity.

17. The method of claim 13, wherein the atmospheric particle detector further comprises an air pump connected to the optical measurement cavity via an airflow port, the method further comprising:

continuously drawing air samples into the optical measurement cavity using the air pump.

18. The method of claim 13, wherein the photodetector is selected from the group consisting of: a photodiode, an avalanche diode, a photomultiplier tube, and combinations thereof.

19. The method of claim 13, wherein an inner surface of the optical measurement cavity is lined with a super hydrophobic coating.

20. The method of claim 19, wherein the super hydrophobic coating comprises a fluoroalkylsilane selected from the group consisting of: 3,3,3-trifluoropropyl trichlorosilane, (tridecafluoro-1,1,2,2-tetrahydrooctyl) trichlorosilane, (heptadecafluoro-1,1,2,2-tetrahydrodecyl) trichlorosilane, and combinations thereof.

* * * * *